United States Patent [19]

Van Brunt

[11] Patent Number: 5,175,357

[45] Date of Patent: Dec. 29, 1992

[54] PROCESS FOR RECOVERING ACETIC ACID FROM AQUEOUS ACETIC ACID SOLUTIONS

[75] Inventor: Vincent Van Brunt, Columbia, S.C.

[73] Assignee: The University of South Carolina, Columbia, S.C.

[21] Appl. No.: 663,299

[22] Filed: Feb. 28, 1991

Related U.S. Application Data

[63] Continuation of Ser. No. 496,437, Mar. 20, 1990, abandoned.

[51] Int. Cl.⁵ ............... C07C 51/48; C07C 121/407
[52] U.S. Cl. ................................. 562/513; 562/608
[58] Field of Search ........................... 562/513, 608

[56] References Cited

U.S. PATENT DOCUMENTS 3,980,701 9/1976 Grinstead ........................ 562/608

OTHER PUBLICATIONS

Deible, Jr., R. W. and Van Brunt, V., "Preliminary Evaluation of Alternatives for Distillation for Acetic Acid Recovery from Terephthalic Acid Flowsheets", presented at the Sixth Symposium on Separation Science for Energy Applications, Knoxville, Tenn., Oct. 23, 1989.
King, C. J., "Acetic Acid Extraction", in Handbook of Solvent Extraction, T. C. Lo, M. H. I. Baird, and C. Hanson, eds. 1983, Chap. 18.5, pp. 567-572.
King, C. J., "Separation Processes Based on Reversible Chemical Complexation", in Handbook of Separation Process Technology, Rousseau, R. W. ed. 1987, Chap. 15, pp. 760-774.
Rickleton, W. A. and Boyle, R. J., "Solvent Extraction with Organophosphines-Commercial and Potential Applications", Separation Science and Technology, vol. 23, pp. 1227-1250 (1988).
Wardell, J. M. and King, C. J., "Solvent Equilibria for Extraction of Carboxylic Acids from Water", J. of Chemical and Engineering Data, vol. 23, pp. 144-148 (1978).
Kertes, A. S. and King, C. J., "Extraction Chemistry of Fermentation Product Carloxylic Acids", Biotechnology and Bioengineering, vol. 28, pp. 269-282 (1986).
Ricker, N. L., Michaels, J. N. and King, C. J., "Solvent Properties of Organic Bases for Extraction of Acetic Acid from Water", J. Separ. Proc. Technol., 1, pp. 36-41 (1979).
Ricker, N. L., Pittman, E. F. and King, C. J., "Solvent Extraction with Amines for Recovery of Acetic Acid from Dilute Aqueous Industrial Streams", J. Separ. Proc. Technol., 1, pp. 23-30 (1980).
Spala, E. E. and Ricker, N. L., "Thermodynamic Model for Solvating Solutions with Physical Interactions", Ind. Eng. Chem. Process Des. Dev., vol. 21, pp. 409-415 (1982).

*Primary Examiner*—Arthur C. Prescott
*Attorney, Agent, or Firm*—Brumbaugh, Graves, Donohue & Raymond

[57] ABSTRACT

A process for recovering acetic acid from an aqueous acetic acid solution comprises contacting the solution with a solvent comprising a diluent component and an extractant component. The extractant component is selected from the group consisting of di-2,4,4-trimethylpentyl-n-octyl phosphine oxide, tri-2,4,4-dimethylpenthyl phosphine oxide and mixtures thereof, and the diluent component comprises at least one high molecular weight ketone. This invention is useful in recovering acetic acid from both low concentration and concentrated aqueous acetic acid streams, and is particularly useful in recovering acetic acid from aqueous acetic acid waste streams in processes for the production of terephthalic acid and cellulose acetate.

16 Claims, 5 Drawing Sheets

PROCESS FOR RECOVERING ACETIC ACID FROM AQUEOUS ACETIC ACID SOLUTIONS

This application is a continuation of application Ser. No. 07/496,437, filed on Mar. 20, 1990, now abandoned.

BACKGROUND OF THE INVENTION

This invention relates to a process for recovering acetic acid from aqueous acetic acid solutions. More particularly, this invention relates to a process for selectively recovering acetic acid from aqueous acetic acid solutions by contacting such solutions with a solvent comprising an extractant component and a diluent component, the extractant component being selected from the group consisting of di-2,4,4-trimethylpentyl-n-octyl phosphine oxide, tri-2,4,4-trimethylpentyl phosphine oxide and mixtures thereof, and the diluent component comprising at least one high molecular weight ketone.

Numerous chemical processes use and produce aqueous process streams comprising acetic acid. As a result, various processes for recovering acetic acid from aqueous acetic acid solutions are known to those skilled in the art. Many of these processes employ distillation techniques, which have substantial equipment and energy costs associated with them. In view of the foregoing, various extraction techniques to replace and/or supplement distillation as a means for acetic acid recovery have previously been developed. For example, King, C. J., "Separation Processes Based on Reversible Chemical Complexation", in *Handbook of Separation Process Technology*, Chap. 15, pp. 760-74 (R. W. Rousseau ed. 1987) and King, C. J., "Acetic Acid Extraction", in *Handbook of Solvent Extraction*, Chap. 18.5, pp. 567-72 (T. C. Lo, M.H.I. Baird & C. Hanson eds. 1983) discuss the use of various solvents comprising an extractant component and a diluent component for extraction of acetic acid from low concentration aqueous acetic acid solutions (i.e. solutions having an acetic acid concentration of about 1.0 weight percent or less), including the use of solvents comprising trioctyl phosphine oxide (TOPO) as an extractant and various ketones as diluents.

However, many acetic acid process streams found in industrial processes are concentrated aqueous acetic acid solutions (i.e. solutions having an acetic acid concentration greater than about 1.0 weight percent). It is well known by those skilled in the art that the extraction properties of a solvent may be quite different at low and high solute concentrations, and that ordinarily the extraction properties of a solvent in high solute concentration systems cannot be inferred from the solvent's behavior in low solute concentration systems. This is due to the fact that, in liquid-liquid systems, the liquid-liquid equilibria tie lines may level out at high solute concentrations. It would therefore be advantageous to be able to use an extraction technique to extract acetic acid from both low concentration and concentrated aqueous solutions. Moreover, it would be extremely advantageous, in employing an extraction process to extract acetic acid from such aqueous acetic acid solutions, to use a solvent which readily differentiates between acetic acid and water, thereby avoiding the extraction of large quantities of water together with acetic acid, and the associated equipment and energy costs involved in downstream water separation.

It is one object of this invention to provide a process wherein the use of distillation techniques in recovering acetic acid from an aqueous solution thereof is minimized. It is a feature of this invention that acetic acid is selectively recovered from an aqueous solution thereof by contacting the solution with a solvent comprising an extractant component present in a concentration of at least 10 weight percent which is selected from the group consisting of di-2,4,4-trimethylpentyl-n-octyl phosphine oxide, tri-2,4,4-trimethylpentyl phosphine oxide, and mixtures thereof, and a diluent component comprising at least one high molecular weight ketone. This invention is advantageous in that it avoids or minimizes the use of expensive and energy intensive distillation techniques in the recovery of acetic acid from aqueous solutions thereof.

It is another object of this invention to provide a process for selectively recovering acetic acid from low concentration and concentrated aqueous acetic acid solutions, including those associated with high purity applications such as acetic acid production. It is a feature of this invention that it selectively recovers acetic acid from such aqueous acetic acid solutions.

It is another object of this invention to provide a process for recovering acetic acid from an aqueous acetic acid solution wherein the amount of water extracted from solution with the acetic acid is minimized due to the selectivity of the solvent used. It is a feature of this invention that the solvent employed selectively extracts acetic acid from an aqueous acetic acid solution. The solvent used in this invention is further advantageous in that it tends to avoid reaction with other constituents in a given process and does not accumulate therein.

Various industrial processes yield aqueous waste or by-product steams containing acetic acid, and thus employ methods for recovering acetic acid from such streams. For example, the most widely used process for the production of terephthalic acid (PTA), a purified intermediate product used in the manufacture of polyester fiber and dimethylterephthalate polymer for plastic bottles, entails the reaction of p-xylene and oxygen in an acetic acid solution. The process requires the purification of an aqueous acetic acid process stream for solvent recovery. Although initial distillation of water from the acid stream recovers most of the acid, the aqueous waste stream from the distillation operation still contains appreciable acetic acid. Traditionally, recovery of the remaining acid from the waste stream has been accomplished through azeotropic distillation, which is an energy intensive operation. It would therefore be advantageous to employ a less energy intensive means for recovering acetic acid from aqueous waste process streams in the above-described PTA process.

It is another object of this invention to provide a process for recovering acetic acid from an aqueous waste process stream in a PTA production process. It is a feature of this invention that the aqueous waste process stream is contacted with the solvent of this invention to extract acetic acid from the process stream. This is advantageous in that it avoids the use of energy-intensive azeotropic distillation to recover acid from the waste stream. This invention may be employed with additional downstream processing steps such as distillation and stripping to further purify the acetic acid recovered from the waste stream.

Another commercial process requiring large amounts of acetic acid is the process for production of cellulose acetate (CA). A widely used process for the production of CA employs an acetylation mixture consisting of acetic anhydride, acetic acid, and sulfuric acid, which is reacted with cellulose to form CA. Recovery of acetic acid is typically achieved by solvent extraction of acetic acid from water followed by distillation of the solvent to separate out acetic acid. However, the solvent typically employed also extracts water which must also be distilled.

Furthermore, usually the solvent employed has a lower boiling point than acetic acid, thus necessitating vaporization of all the solvent. However, coextraction of the water by existing solvent technology substantially increases the energy requirements of the current solvent recovery-acid purification distillation. It would thus be advantageous to minimize the amount of water coextracted in an acetic acid recovery process employed in a CA production process.

It is yet another object of the is invention to provide a process for recovering acetic acid from the aqueous acetic acid waste stream in a process for production of CA. It is a feature of this invention that only a small amount of water is co-extracted from the waste stream, thus advantageously reducing equipment and energy costs in the CA process.

SUMMARY OF THE INVENTION

This invention provides a process for selectively recovering acetic acid from an aqueous acetic acid solution. The process comprises contacting an aqueous acetic acid solution with a solvent having a diluent component and an extractant component, the extractant component preferably being present in a concentration of at least 5 weight percent, based upon the total weight of the solvent. The extractant component is selected from the group consisting of di-2,4,4-trimethylpentyl-n-octyl phosphine oxide, tri-2,4,4-trimethylpentyl phosphine oxide, and mixtures thereof, preferably a mixture of a major amount of di-2,4,4-trimethylpentyl-n-octyl phosphine oxide and a lesser amount of tri-2,4,4-trimethylpentyl phosphine oxide. The diluent component comprises at least one high molecular weight ketone preferably selected from the group consisting of diisobutyl ketone, dimethyl heptanone, octanone and mixtures thereof.

In one preferred embodiment, this invention may be employed in a process for the production of terephthalic acid to recover acetic acid from an aqueous acetic acid waste stream. In another preferred embodiment this invention may be employed in a process for the production of cellulose acetate to recover acetic acid from an aqueous acetic acid waste stream.

This invention is useful in both low concentration and concentrated aqueous acetic acid solutions, and is particularly advantageous in selectively recovering acetic acid from concentrated aqueous acetic acid solutions. This invention is advantageous over distillation separation techniques in that it is less energy and equipment intensive than such techniques. This invention is advantageous over other liquid-liquid separation techniques for recovering acetic acid from aqueous streams in that it exhibits a high degree of selectivity in recovering acetic acid, thus minimizing water carryover to the solvent. In addition, the solvent employed in this invention is non-reactive with other compounds present in the process wherein employed, and thus does not accumulate in the process acid recovery stream.

DESCRIPTION OF THE PREFERRED EMBODIMENTS

The aqueous acetic acid solutions treated in accordance with this invention may have a wide range of acetic acid concentrations. For example, this invention may be employed in conjunction with "low concentration" aqueous acetic acid solutions (i.e. solutions having an acetic acid concentration of about 1.0 weight percent or less). In addition, this invention is useful in recovering acetic acid from "concentrated" acetic acid solutions (i.e. solutions having acetic acid concentrations greater than about 1.0 weight percent), such as CA process streams typically having acetic acid concentrations up to about 35 weight percent, and PTA process streams typically having concentrations up to about 65 weight percent. The aqueous acetic acid solutions treated in accordance with this invention may also comprise various inorganic cations and other impurities.

The extractant component of the solvent used in this invention is selected from the group consisting of di-2,4,4-trimethylpentyl-n-octyl phosphine oxide, tri-2,4,4trimethylpentyl phosphine oxide, and mixtures thereof, preferably a mixture of a major amount of di-2,4,4-trimethylpentyl-n-octyl phosphine oxide and a minor amount of tri-2,4,4-trimethylpentyl phosphine oxide. In a particularly preferred embodiment, the extractant is a mixture of about 85 weight percent di-2,4,4-trimethylpentyl-n-octyl phosphine oxide and about 15 weight percent tri-2,4,4-trimethylpentyl phosphine oxide. Such an extractant is available, for example, from American Cyanamid Company under the CYANEX 925 trade name.

The use of CYANEX 925 to extract various metals from acid solutions is disclosed in Rickleton, W. A. & Boyle, R. J. "Solvent Extraction with Organophosphines—Commercial & Potential Applications," Separation Science & Technology, Vol. 23, pp. 1227-50 (1988). However, the application of CYANEX 925 to extract metals from acid solutions is distinguishable from this invention in several respects. First, the process of this invention employs a solvent which has a synergistic selective affinity for an organic component (i.e. acetic acid) extraction from an aqueous medium, and the mechanisms for metal and organic component extraction are clearly distinct. In addition, this invention is effective in achieving acetic acid extraction from concentrated aqueous acetic acid solutions.

The diluent component of the solvent used in this invention comprises at least one high molecular weight ketone. As used in this description and in the appended claims, the term "high molecular weight ketone" refers to ketones having a molecular weight of at least about 100. Such ketones have boiling points above that of acetic acid. The high molecular weight ketone is preferably selected from the group consisting of diisobutyl ketone (DIBK), dimethyl heptanone, octanone, and mixtures thereof. In one particularly preferred embodiment, the diluent is substantially pure DIBK. In another particularly preferred embodiment, the diluent comprises a mixture of a major amount of DIBK and a lesser amount of dimethylheptanone, preferably 2,4-dimethyl-6-heptanone. The diluent may also comprise minor amounts of other compounds such as alcohols, glycols, esters, and the like.

The solvent preferably comprises at least about 5 weight percent of the above-described extractant, with the balance of the solvent preferably being made up of the above-described diluent. This is because, as discussed hereinbelow, at above about 5-10 weight percent extractant in the solvent, a synergistic effect has been observed between the extractant and diluent components, and addition of extractant to the solvent has the combined advantageous effect of both decreasing the solvent loss to the aqueous phase and decreasing the loading of water in the solvent, thereby increasing the efficiency of the separation of acetic acid from the aqueous solution.

As set forth below, various examples of the solvents to be used in this invention were prepared at a variety of extractant concentrations, and contacted with aqueous acetic acid solutions in accordance with this invention. These examples are merely illustrative, and not meant to limit the invention in any way.

All chemicals used to prepare the various solvents were used in the condition supplied, without further purification. Technical grade diisobutyl ketone (DIBK) was obtained from Aldrich Chemical Company and a mass spectrometry analysis determined it to be 71.2% DIBK, 23.7% 2,4-dimethyl-6-heptanone, and 5.1% of a C alcohol. ChemService, Inc. supplied the standards grade DIBK and their analysis showed it to be 96% DIBK, with 96% purity being the highest purity readily available. The extractant used was CYANEX 925, and furnished by American Cyanamid Company. CYANEX 925 is a mixture of 85% di-2,4,4-trimethylpentyl-noctyl phosphine oxide and 15% tri-2,4,4-trimethylpentyl phosphine oxide. The glacial acetic acid was supplied by Fisher Scientific Company, and deionized water was used in the aqueous solutions. The terephthalic acid (PTA) stream solution was supplied from a terephthalic acid flowsheet feed solution from an operating plant. Plant samples taken over a three week period were analyzed by GC-Mass Spectrometry and determined to contain no significant variation in composition.

All concentrations were measured with a Hewlett-Packard Model 5840A gas chromatograph equipped with an integrator and a thermal conductivity detector. The column was a SUPELCO 80/120 mesh CARBOPACK B/3% SP-1500 packed column with a recommended use for organic solvents. An injection temperature of 230° C. and a detector temperature of 260° C. were used for each run. The carrier gas was helium with a flow rate of 60 ml/min. The oven temperature was programmed initially be 125° C. for 36 seconds and then ramped to 210° C. at a rate of 30° C./minute. Peak areas were converted to weight fractions by comparison to the areas determined by external standards for the aqueous phase and for the organic phase. Since the extractant (CYANEX 925) concentration could not be measured on the GC and its solubility in water is extremely low, it was assumed that all the extractant was in the organic layer. The maximum difference from the actual calibrated mass fraction in a series of runs was usually less than 5%.

Distribution coefficient ($K_D$) values for acetic acid and water were calculated from the weight percents as follows:

$$K_D = \frac{(X_A)\text{org}}{(X_A)\text{aq}}$$

where $(X_A)$org and $(X_A)$aq are the weight percent concentrations in the organic and aqueous phases, respectively.

For each extraction experiment, a known concentration of an aqueous acetic acid solution was mixed with a known organic phase in a 50 ml stoppered flask. The total volume of both solutions was consistently about 30 ml. The flasks were turned over about 20 times by hand at room temperature. Further experiments with agitation by a magnetic stirrer for 12 hours confirmed that the above-described technique was adequate. The phases separated easily and were allowed to settle for 2 hours before analysis.

In these experiments, three different solutions were analyzed. An aqueous solution of 60.0% acetic acid was contacted with an organic phase of extractant (i.e. CYANEX 925) and two different diluents (i.e. 96% purity DIBK and technical grade DIBK). For these solutions, the initial solvent to feed ratio was 1 to 3. The third solution tested was an acetic acid aqueous solution from an industrial terephthalic acid production process. This solution was contacted with the technical grade DIBK solution only, with a solvent to feed ratio of 1 to 1.

Figure 1:
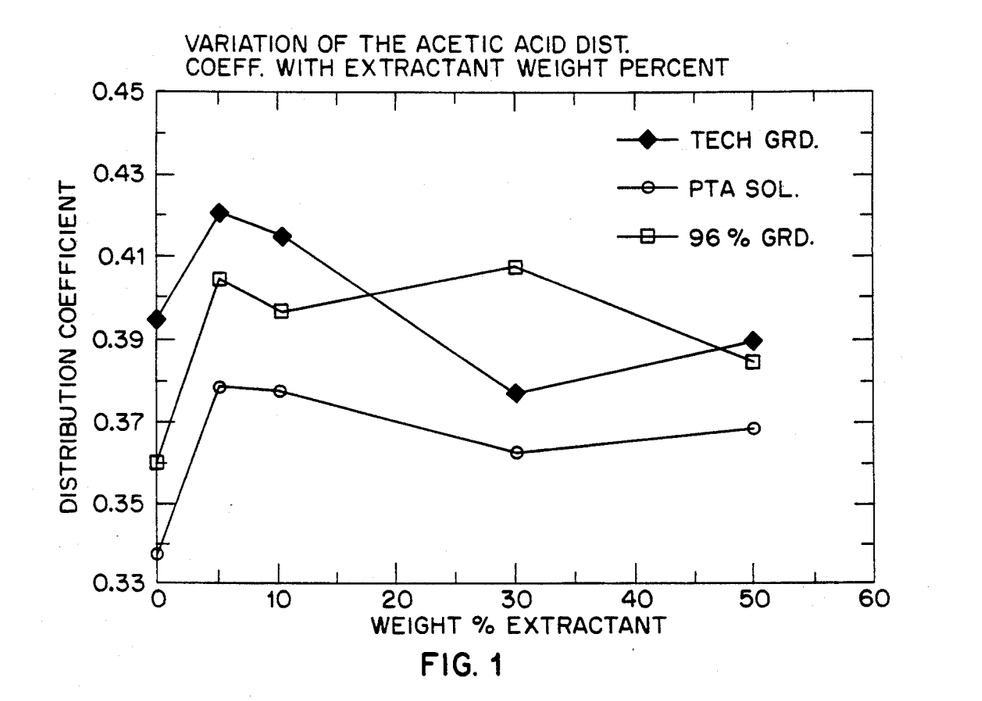
FIG. 1 shows the variation of the acetic acid distribution coefficient $K_D$ as a function of the concentration of extractant in the solvent.

FIG. 1 shows the effect of varying the concentration of extractant on the extraction of acetic acid for the three solutions. This figure shows that $K_D$ reached a maximum at 5 wt. % extractant and than declined slightly. Also, the $K_D$ for the technical grade DIBK solution was higher than the 96% grade DIBK and the PTA solutions, except at 30 wt. % extractant. At this concentration, the 96% grade DIBK $K_D$ was higher than the others and was the maximum $K_D$ for this solution. The isomer in the technical grade solution that improved the extraction of acid at lower concentrations no longer improved the $K_D$ after about 18 wt. % extractant, and at 50 wt. % the $K_D$ values were about the same.

Figure 2:
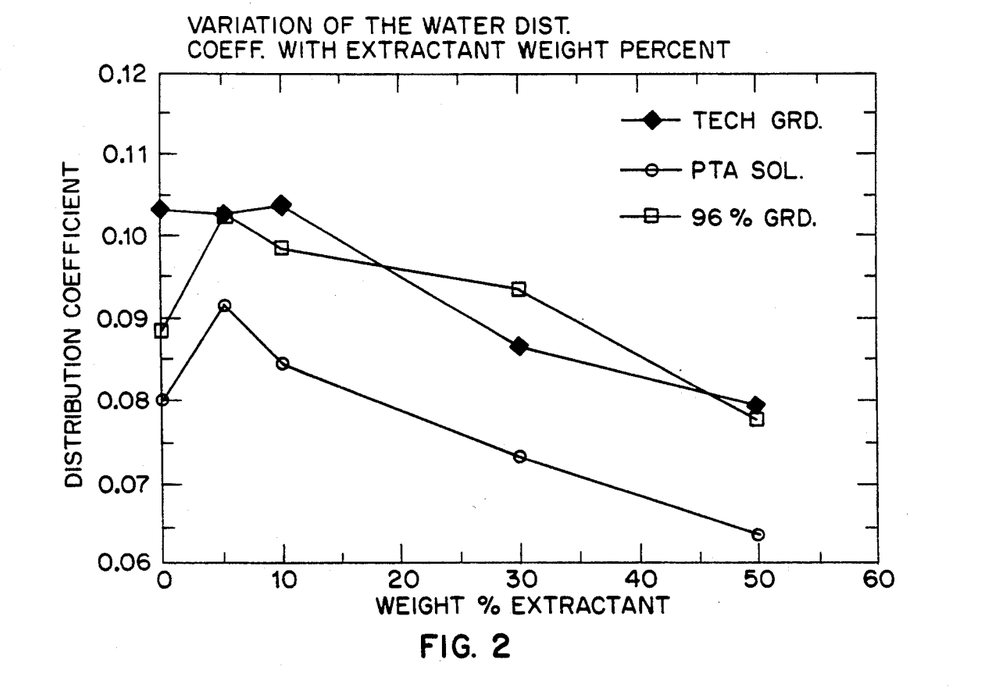
FIG. 2 shows the variation of water distribution coefficient $K_D$ as a function of the concentration of extractant in the solvent.

The effect of extractant concentration on the water $K_D$ was similar to the effect on the acid $K_D$. FIG. 2 shows $K_D$ was largest with the technical grade DIBK and smallest with the TPA solution. Again at 30 wt. % extractant, the 96% grade DIBK $K_D$ was the highest.

The selectivity, $\beta$, of an extractant is defined as:

$$\beta = \frac{(K_D)\text{acid}}{(K_D)\text{water}}$$

Figure 3:
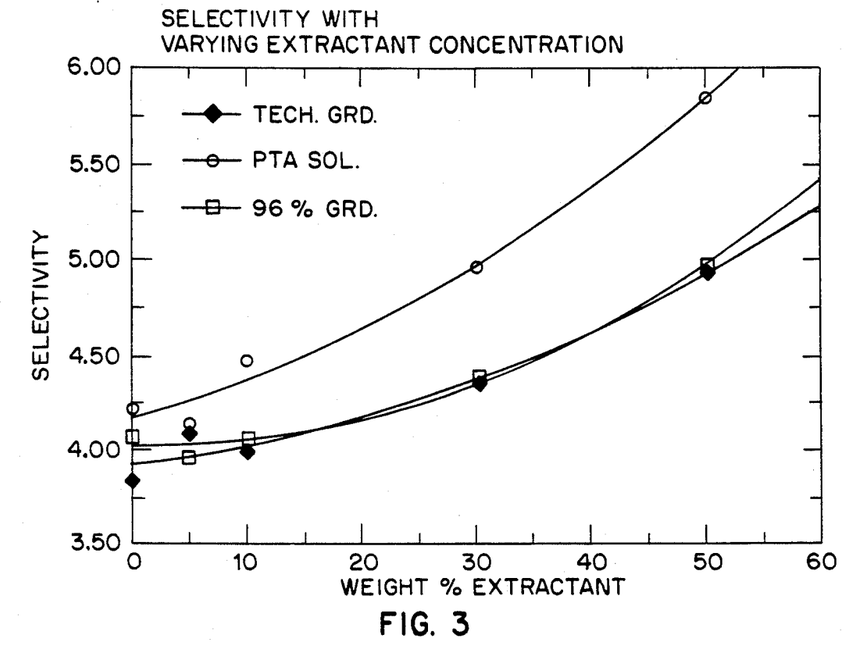
FIG. 3 shows the variation of acetic acid selectivity as a function of the concentration of extractant in the solvent.

The variation of selectivity with extractant concentration is shown in FIG. 3. The selectivity increased with increasing extractant concentration with the selectivity of the PTA solution largest at all concentrations. The selectivities for the technical and 96% grade DIBK solutions were very similar.

Figure 4:
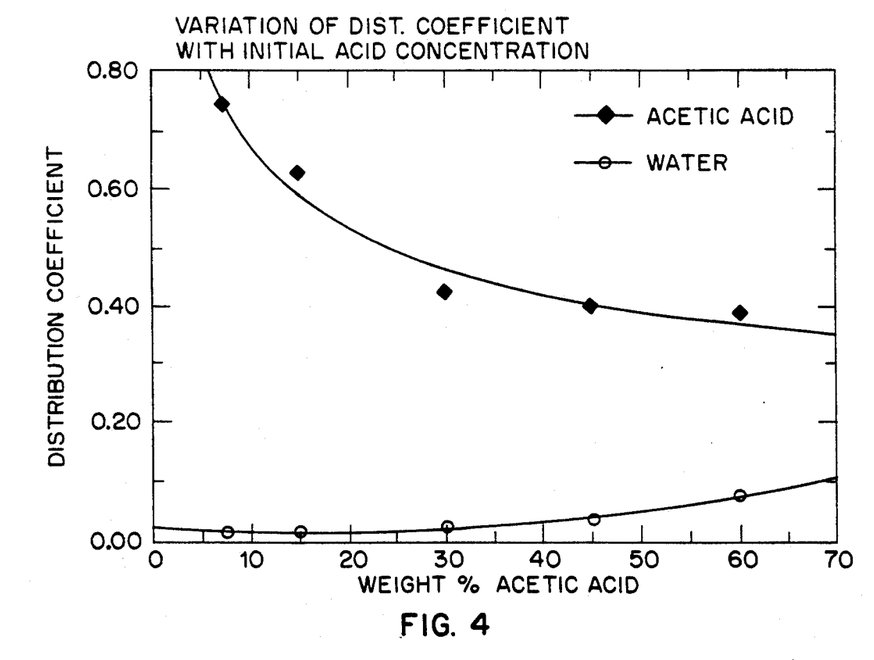
FIG. 4 shows the variation of the distribution coefficients for acetic acid and water as a function of initial acetic acid concentration.
Figure 5:
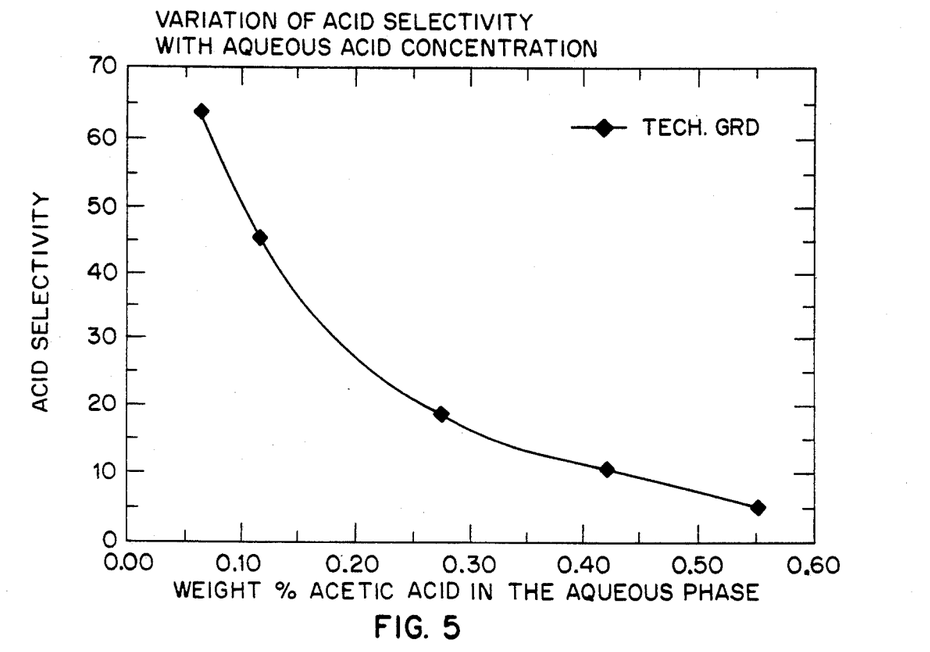
FIG. 5 shows the variation of acetic acid selectivity as a function of aqueous acetic acid concentration.
Figure 6:
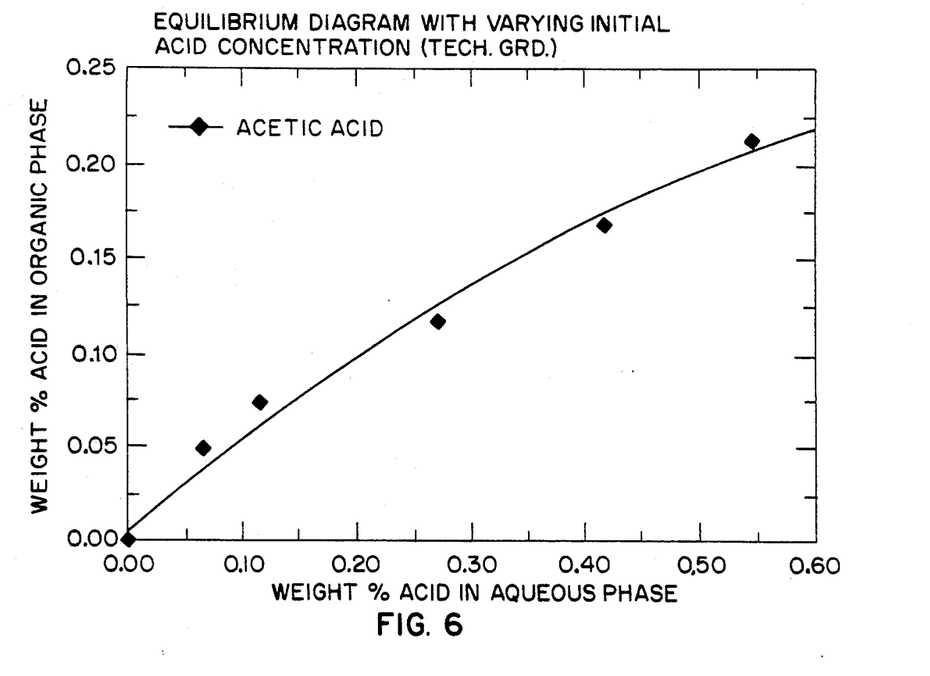
FIG. 6 shows the extraction equilibria curve for acetic acid distributed in an aqueous phase and an organic phase in a solvent made up of 50 weight percent CYANEX 925 and 50 weight percent technical grade DIBK.

The effect of acetic acid concentration on $K_D$ and selectivity was also studied. An organic phase of 50 wt. % DIBK and 50 wt. % extractant was contacted with aqueous solutions of varying acetic acid concentrations. In FIG. 4 the $K_D$ for acetic acid is shown as having decreased with increasing aqueous acid concentrations. The decrease was greater below 30 wt. % acid. For water, the $K_D$ gradually increased with increasing acid concentration. Therefore, at low acid concentrations, the solvent was very selective in extracting acetic acid over water, as shown in FIG. 5. The selectivity decreased with increasing acid concentration, with the decrease being more rapid at lower acid concentrations. FIG. 6 shows that the equilibrium diagram for the technical grade DIBK solution has an upward curvature, reflecting the decrease in $K_D$ with increasing acid concentration.

Figure 7:
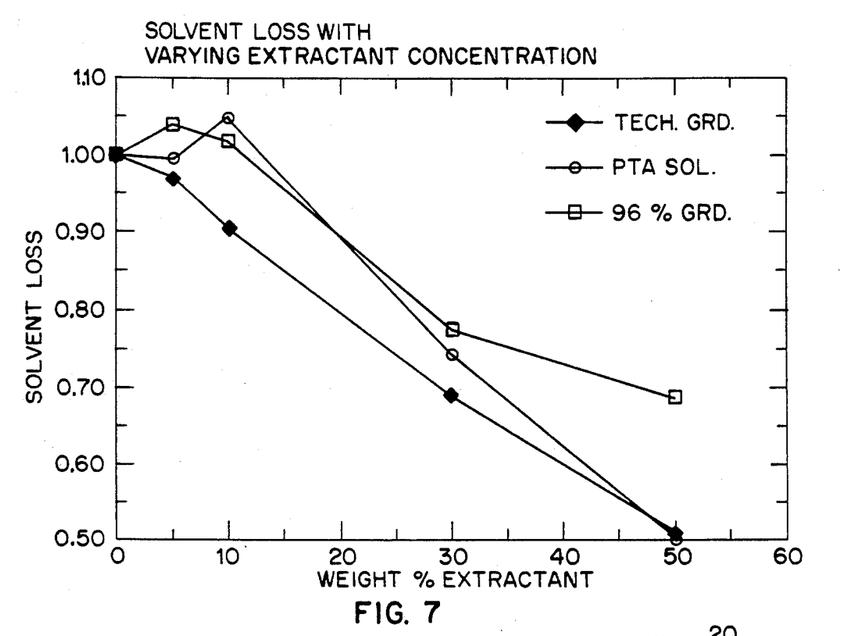
FIG. 7 shows the variation of solvent loss as a function of extractant concentration.

An important factor in any extraction process is the amount of solvent lost to the aqueous phase. Minimizing solvent loss increases the efficacy of a given extraction process. FIG. 7 shows that, above about 10 wt. % extractant in the solvent, the amount of solvent lost decreased with increasing extractant concentration. Except for the 10 wt. % concentration, the 96% grade solution had the highest solvent loss while the PTA solution had the lowest solvent loss.

In summary, below about 5-10 wt. % extractant in the solvent there was little effect on solvent loss or the $K_D$ values, but at above about 10 wt. % extractant concentration in the solvent, increasing the extractant concentration decreased the solvent loss, decreased the water $K_D$, slightly decreased the acetic acid $K_D$, and increased the acid selectivity.

While not wishing to be bound by any one theory, it is believed that the above-described results were obtained because the extractant complexes with the acid in the aqueous phase, complexes with water in the aqueous phase, and simultaneously complexes with the DIBK in the organic phase. Below about 5-10 wt. % extractant concentration in the solvent, adding extractant to the DIBK has little effect on $K_D$ or $\beta$ because the extractant concentration is too low. Above about 5-10 wt. % extractant in the solvent, however, the extractant readily complexes with the DIBK in the organic phase, thus preventing it from complexing with water in the organic phase. This is advantageous because water is prevented from being extracted into the organic phase and DIBK is prevented from being lost to the aqueous phase. Because acetic acid is a stronger acid than water, acetic acid is able to complex with the extractant and the DIBK to be extracted into the organic phase. The selectivities are high because acetic acid is extracted into the organic phase but water is not. As the aqueous acid phase concentration increases, the aqueous phase becomes more similar to the organic phase and therefore the acetic acid $K_D$ decreases, the water $K_D$ increases, and the selectivity decreases. The above-described hypothesized complexing mechanism is based upon experimental results for solvent compositions having extractant component concentrations greater than about 5 wt. %. However, it is possible that solvent component interactions may take place at extractant concentrations lower than about 5 wt. %, although such concentrations were not experimentally determined in the above-described experiments.

Figure 8:
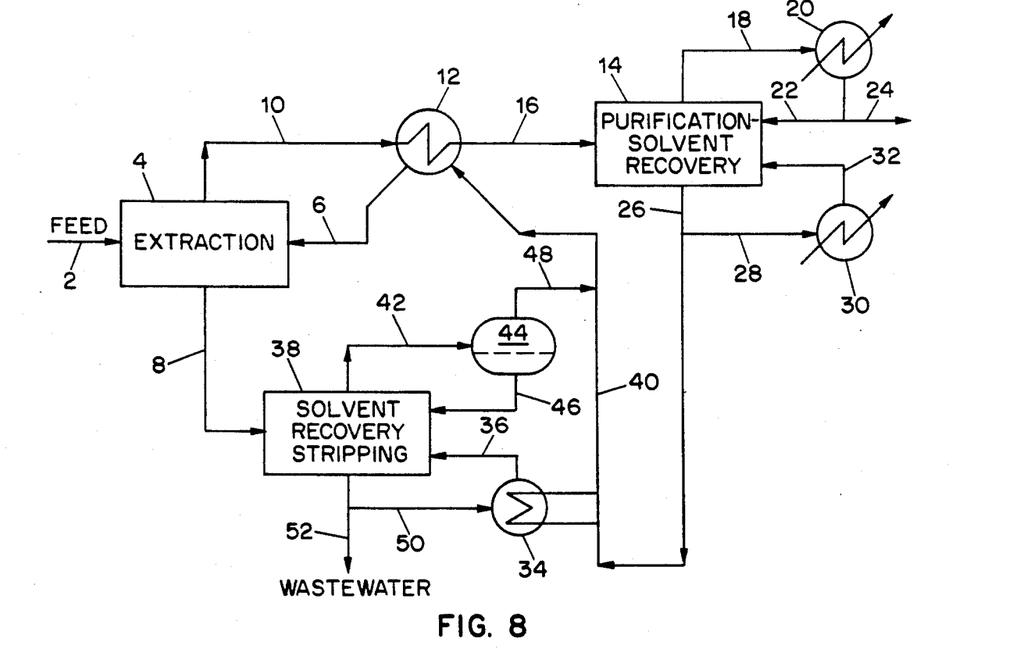
FIG. 8 shows a process flow diagram for one embodiment of this invention for acetic acid recovery.

FIG. 8 depicts a process flowsheet showing a preferred embodiment of this invention wherein this invention is employed to recover acetic acid from an aqueous acetic acid process stream, such as in a PTA or CA production process. In FIG. 8, an aqueous acetic acid feed stream 2 (typically originating from a previous initial distillation of the aqueous acetic acid stream which is a by-product of the PTA production process or a previous filtration of the aqueous acetic acid stream which is a by-product of the CA production process) enters extraction unit 4, in which feed stream 2 is countercurrently contacted with solvent comprising a diluent component and at least 10 wt. % of an extractant component, as hereinabove described. The solvent enters extraction unit 4 through line 6. A primarily aqueous stream containing residual amounts of acetic acid and solvent exits the bottom of extraction unit 4 through line 8 for further processing, as discussed hereinbelow. The acetic acid-rich solvent stream, which may contain small amounts of water, exits extraction unit 4 through overhead line 10 and passes through heat exchanger 12, where it is preheated prior to entering the purification-solvent recovery (PSR) unit 14 through line 16. PSR unit 14 may be operated at subambient pressures in the range of 10 mm Hg to atmospheric pressure. Such pressures may be achieved, for example, by employing jet ejectors or mechanical pumps, as is well known to those skilled in the art. In PSR unit 14, acetic acid and any water are separated out and exit through overhead line 18, and are thereupon sent to condenser 20. All or a portion of the acetic acid/water stream exiting condenser 20 may be recycled to PSR unit 14 through line 22, or carried by means of line 24 for further downstream processing, including use for further production of PTA or CA.

Purified solvent exits PSR unit 14 at its bottom through line 26. A portion of the purified solvent may be recycled through line 28 to reboiler 30 and line 32 to PSR unit 14. Remaining purified solvent passes through line 26 to reboiler 34; however, all or a portion of purified solvent may bypass reboiler 34 and be directed through lines 26 and 40 to heat exchanger 12 and ultimately enters extraction unit 4 through line 6 for counter-current contacting with feed stream 2, as previously described.

The primarily aqueous stream containing residual amounts of acetic acid and solvent which exits extraction unit 4 through line 8 is fed to SRS unit 38, which is a distillation column which strips any organic materials from the aqueous stream. Primarily organic materials exit SRS unit 38 through overhead line 42, which feeds into decanter 44. Decanter 44 separates out any remaining water, which is returned to SRS unit 38 through line 46. The organic phase (i.e. solvent) leaves decanter 44 through overhead line 48, for eventual recycle to extraction unit 4, as shown. Water exits from the bottom of SRS unit 38 through line 52 for eventual combination with other wastewater streams and/or further downstream processing. All or a portion of the water exiting SRS unit 38 may be recycled to SRS unit 38, as shown.

Figure 9:
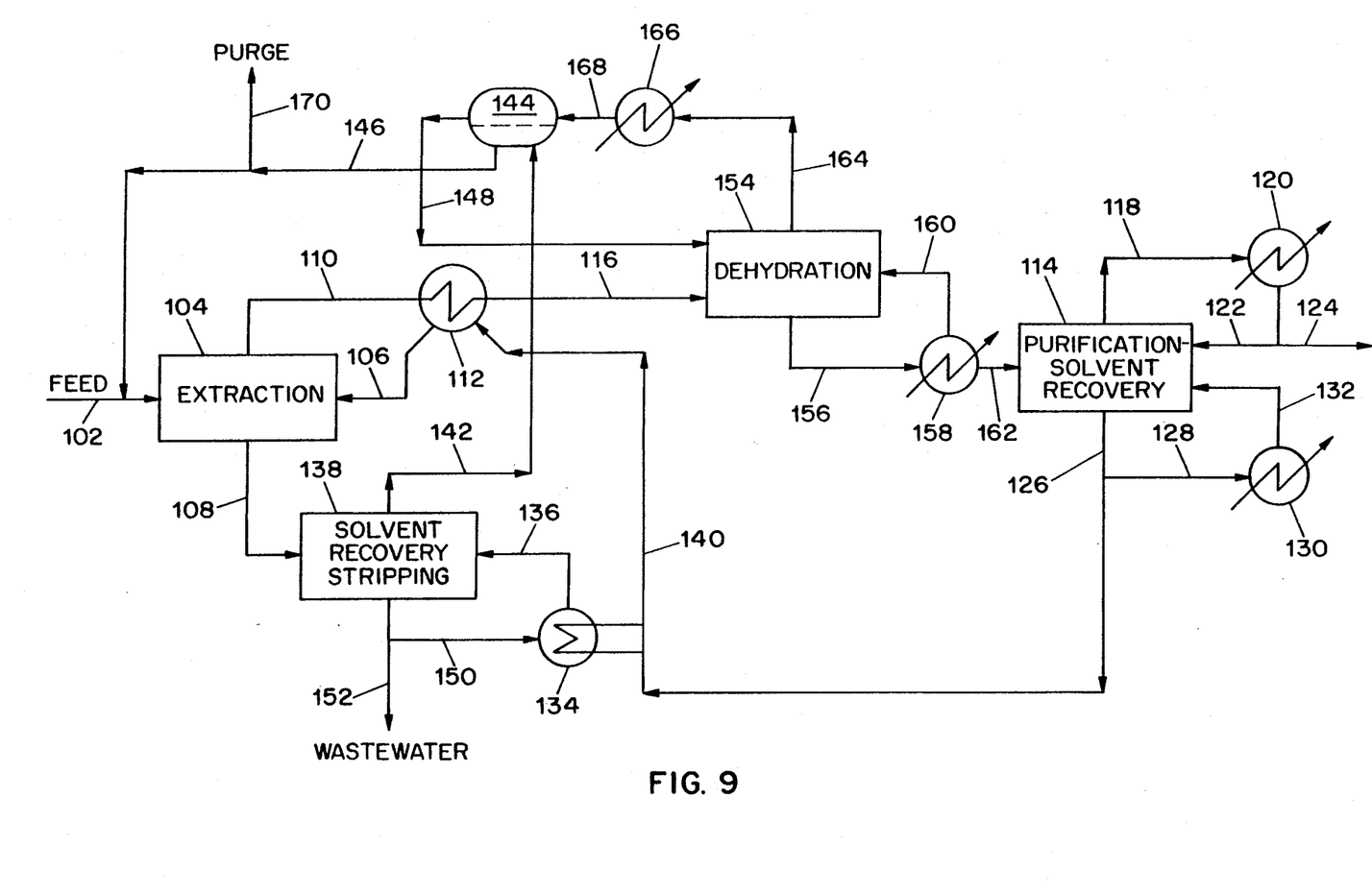
FIG. 9 shows a process flow diagram for another embodiment of this invention for acetic acid recovery.

FIG. 9 depicts a process flowsheet showing another preferred embodiment of this invention wherein this invention is employed to recover acetic acid from an aqueous acetic acid process stream, such as in a PTA or CA production process. This embodiment is particularly useful in situations where higher purity recovered acetic acid is desired or required. In FIG. 9, an aqueous acetic acid feed stream 102 (typically originating from a previous initial distillation of the aqueous acetic acid stream which is a by-product of the PTA production process or a previous filtration of the aqueous acetic acid stream which is a by-product of the CA production process) enters extraction unit 104, in which feed stream 102 is countercurrently contacted with solvent comprising a diluent component and at least 10 wt. % of an extractant component, as hereinabove described. The solvent enters extraction unit 104 through line 106. A primarily aqueous stream containing residual amounts of acetic acid and solvent exits the bottom extraction unit 104 through line 108 for further processing, as discussed hereinbelow. The acetic acid-rich solvent stream, which may contain small amounts of water, exits extraction unit 104 through overhead line 110 and passes through heat exchanger 112, where it is preheated prior to entering dehydration tower 154 through line 116. Dehydration tower 154 is employed to reduce water and intermediate boiling components in the solvent. The presence of dehydration tower 154, particularly the rectification section therein, permits the process depicted in FIG. 9 to have a scrubbing capability to reduce the coextracted water and intermediate boiling components. Dehydration tower 154 may be operated at subambient pressures in the range of 10 mm Hg to atmospheric pressure. Such pressures may be achieved, for example, by employing jet ejectors or mechanical pumps, as is well known to those skilled in the art. Water and any residual organics (i.e. solvent and/or acetic acid) pass through overhead line 164 to condenser 166 and through line 168 to decanter 144. Decanter 144 separates out any water, which is returned to feed 102 by means of line 146, and/or purged (together with any impurities or unwanted compounds) through line 170. Dehydrated solvent exits dehydration tower 154 through line 156. A portion of the dehydrated solvent may be recycled back to dehydration tower 154 through reboiler 158 and line 160. Remaining dehydrated solvent and acetic acid passes through reboiler 158 and line 162 to purification solvent recovery (PSR) unit 114.

PSR unit 114 may be operated at subambient pressures in the range of 10 mm Hg to atmospheric pressure. Such pressures may be achieved, for example, by employing jet ejectors or mechanical pumps, as is well known to those skilled in the art. In PSR unit 114, any acetic acid and/or water are separated out and exit through overhead line 118, and are thereupon sent to condenser 120. All or a portion of the acetic acid/water stream exiting condenser 120 may be recycled to PSR unit 114 through line 122, or carried by means of line 124 for further downstream processing, including use for further production of PTA or CA.

Purified solvent exits PSR unit 114 at its bottom through line 126. A portion of the purified solvent may be recycled through line 128 to reboiler 130 and line 132 to PSR unit 114. Remaining purified solvent passes through line 126 to heat exchanger 134; however, all or a portion of the purified solvent may bypass heat exchanger 134 and be directed through lines 126 and 140 to heat exchanger 112 and ultimately enters extraction unit 104 through line 106 for counter-current contacting with feed stream 102, as previously described.

The primarily aqueous stream containing residual amounts of acetic acid and solvent which exits extraction unit 104 through line 108 is fed to SRS unit 138, which is a distillation column which strips any organic materials from the aqueous stream. Primarily organic materials exit SRS unit 138 through overhead line 142, which feeds into decanter 144. Decanter 144 separates out any remaining water, which is recycled to feed line 102 and/or purge line 170 through line 146. Rectification as provided by the combination of SRS unit 138 and decanter 144 permits the intermediate boiling components to have a pathway to purge line 170 through line 146 from decanter 144. The organic phase (i.e. solvent and/or acetic acid) leaves decanter 144 through overhead line 148 for eventual recycle to dehydration tower 154, as shown. Water exits from the bottom of SRS unit 138 through line 152 for eventual combination with other wastewater streams and/or further downstream processing. All or a portion of the water exiting SRS unit 138 may be recycled to SRS unit 138, as shown.

Although this invention has been illustrated by reference to specific embodiments, it will be apparent to those skilled in the art that various changes and modifications may be made which clearly fall within the scope of this invention.

I claim:

1. A process for selectively recovering acetic acid from an aqueous acetic acid solution, comprising contacting a low concentration aqueous acetic acid solution having an acetic acid concentration of about 1.0 weight percent or less or a concentrated aqueous acetic acid solution having an acetic acid concentration of greater than about 1.0 weight percent with a solvent comprising a diluent component and an extractant component, the extractant component selected from the group consisting of di-2,4,4-trimethylpentyl-n-octyl phosphine oxide, tri-2,4,4-trimethylpentyl-n-octyl phosphine oxide and mixtures thereof, and the diluent component comprising at least one high molecular weight ketone, wherein selectivity of acetic acid removal is increased, and solvent loss to the aqueous solution and water loading in the solvent are reduced by the presence of the extractant component in a concentration of at least 10 weight percent, based upon the total weight of extractant in the solvent.

2. A process according to claim 1, in which the aqueous acetic acid solution is derived from a process for producing terephthalic acid.

3. A process according to claim 1, in which the aqueous acetic acid solution is derived from a process for producing cellulose acetate.

4. A process according to claim 1, in which the aqueous acetic acid solution additionally comprises inorganic cations.

5. A process according to claim 2, in which the aqueous acetic acid solution has an acetic acid concentration up to about 65 weight percent.

6. A process according to claim 3, in which the aqueous acetic acid solution has an acetic acid concentration up to about 30 weight percent.

7. A process according to claim 1, in which the extractant component is a mixture of a major amount of di-2,4,4-trimethylpentyl-n-octyl phosphine oxide and a minor amount of tri-2,4,4-trimethylpentyl phosphine oxide.

8. A process according to claim 7, in which the extractant component is a mixture of about 85 weight percent di-2,4,4-trimethylpentyl-n-octyl phosphine oxide and about 15 weight percent tri-2,4,4-trimethylpentyl phosphine oxide.

9. A process according to claim 1, in which the diluent component comprises ketones selected from the group consisting of diisobutyl ketone, dimethyl heptanone, octanone and mixtures thereof.

10. A process according to claim 9, in which the diluent component comprises a major amount of diisobutyl ketone and a lesser amount of 2,4-dimethyl-6-heptanone.

11. A process according to claim 9, in which the diluent component is substantially pure diisobutyl ketone.

12. A process according to claim 1, in which the solvent is further processed subsequent to contacting with the aqueous acetic acid solution to recover the acetic acid contained therein.

13. A process for selectively recovering acetic acid in a process for production of terephthalic acid, comprising:
  (a) processing the aqueous acetic acid stream produced during the production of terephthalic acid, to recover a major amount of acetic acid and product a low concentration aqueous acetic acid solution having an acetic acid concentration of about 1.0 weight percent or less or a concentrated aqueous acetic acid waste stream having an acetic acid concentration of greater than about 1.0 weight percent;
  (b) countercurrently contacting the waste stream with a solvent comprising a diluent component and an extractant component, the extractant component selected from the group consisting of di-2,4,4-trimethylpentyl-n-octyl phosphine oxide, tri-2,4,4-trimethylpentyl phosphine oxide and mixtures thereof, and the diluent component comprising at least one high molecular weight ketone, wherein selectivity of acetic acid removal is increased, and solvent loss to the aqueous solution and water loading in the solvent are reduced by the presence of the extractant component in a concentration of at least 10 weight percent, based upon the total weight of extractant in the solvent to produce an acetic acid-rich solvent stream and an acetic acid-lean waste stream;
  (c) stripping acetic acid from the acetic acid-rich and acetic acid-lean solvent streams to recover the acetic acid and solvent contained therein; and
  (d) recycling the recovered solvent for further contacting with the waste stream in accordance with step (b).

14. A process for selectively recovering acetic acid in a process for producing cellulose acetate, comprising:
  (a) processing the aqueous acetic acid stream produced during the production of cellulose acetate, to recover a major amount of acetic acid and produce a low concentration aqueous acetic solution having an acetic concentration of about 1.0 weight percent or less or a concentrated aqueous acetic acid waste stream having an acetic acid concentration of greater than about 1.0 weight percent;
  (b) countercurrently contacting the waste stream with a solvent comprising a diluent component and an extractant component, the extractant component selected from the group consisting of di-2,4,4-trimethylpentyl-n-octyl phosphine oxide, tri-2,4,4-trimethylpentyl phosphine oxide and mixtures thereof, and the diluent component comprising at least one high molecular weight ketone, wherein selectivity of acetic acid removal is increased, and solvent loss to the aqueous solution and water loading in the solvent are reduced by the presence of the extractant component in a concentration of at least 10 weight percent, based upon the total weight of extractant in the solvent to produce an acetic acid-rich solvent stream and an acetic acid-lean waste stream;
  (c) stripping acetic acid from the acetic acid-rich and acetic acid-lean solvent streams to recover the solvent and acetic acid contained therein; and
  (d) recycling the recovered solvent for further contacting with the waste stream in accordance with step (b).

15. A process for selectively for recovering acetic acid in a process for production of terephthalic acid, comprising:
  (a) processing the aqueous acetic acid stream produced during the production of terephthalic acid, to recover a major amount of acetic acid and produce a low concentration aqueous acetic solution having an acetic acid concentration of about 1.0 weight percent or less or a concentrated aqueous acetic acid waste stream having an acetic acid concentration of greater than about 1.0 weight percent;
  (b) countercurrently contacting the waste stream with a solvent comprising a diluent component and an extractant component, the extractant component selected from the group consisting of di-2,4,4-trimethylpentyl-n-octyl phosphine oxide, tri-2,4,4-trimethylpentyl phosphine oxide and mixtures thereof, and the diluent component comprising at least one high molecular weight ketone, wherein selectivity of acetic acid removal is increased, and solvent loss to the aqueous solution and water loading in the solvent are reduced by the presence of the extractant component in a concentration of at least 10 weight percent, based upon the total weight of extractant in the solvent to produce an acetic acid-rich solvent stream and an acetic acid-lean waste stream;
  (c) dehydrating the acetic acid-rich solvent stream to remove any water and intermediate boiling compounds contained therein;
  (d) stripping acetic acid from the dehydrated acetic acid-rich solvent stream and acetic acid-lean solvent stream to recover the solvent and the acetic acid contained therein; and
  (e) recycling the recovered solvent for further contacting with the waste stream in accordance with step (b).

16. A process for selectively recovering acetic acid in a process for production of cellulose acetate, comprising:
  (a) processing the aqueous acetic acid stream produced during the production of cellulose acetate, to recover a major amount of acetic acid and produce a low concentration or concentrated aqueous acetic acid waste stream;
  (b) countercurrently contacting the waste stream with a solvent comprising a diluent component and an extractant component, the extractant component selected from the group consisting of di-2,4,4-trimethylpentyl-n-octyl phosphine oxide, tri-2,4,4-trimethylpentyl phosphine oxide and mixtures thereof, and the diluent component comprising at least one high molecular weight ketone, wherein selectivity of acetic acid removal is increased, and solvent loss to the aqueous solution and water loading in the solvent are reduced by the presence of the extractant component in a concentration of at least 10 weight percent, based upon the total weight of extractant in the solvent to produce an acetic acid-rich solvent stream and an acetic acid-lean waste stream;

(c) dehydrating the acetic acid-rich solvent stream to remove any water and intermediate boiling compounds contained therein;

(d) stripping acetic acid from the dehydrated acetic acid-rich solvent stream and acetic acid-lean solvent stream to recover the solvent and the acetic acid contained therein; and (e) recycling the recovered solvent for further contacting with the waste stream in accordance with step (b).

* * * * *

UNITED STATES PATENT AND TRADEMARK OFFICE
CERTIFICATE OF CORRECTION

PATENT NO. : 5,175,357  
DATED : December 29, 1992  
INVENTOR(S) : Vincent Van Brunt Page 1 of 2

It is certified that error appears in the above-identified patent and that said Letters Patent is hereby corrected as shown below:

Title page, 7th line of ABSTRACT, "hyl" should read --yl--.

Col. 2, line 34, "steams" should read --streams--.

Col. 5, line 50, "C alcohol" should read --$C_6H_{13}OH$ alcohol--.

Col. 3, line 18, "the is" should read --this--.

Col. 5, line 56, "noctyl" should read --n-octyl--.

Col. 6, line 7, "be" should read --to be--.

Col. 6, line 53, "than" should read "then".

Col. 10, line 42, "tri-2,4,4-trimethylpentyl-n-octyl" should read --tri-2,4,4-trimethylpentyl--.

Col. 11, bridging lines 28-29, "product" should read --produce--.

UNITED STATES PATENT AND TRADEMARK OFFICE
CERTIFICATE OF CORRECTION

PATENT NO. : 5,175,357
DATED : December 29, 1992
INVENTOR(S) : Vincent Van Brunt It is certified that error appears in the above-indentified patent and that said Letters Patent is hereby corrected as shown below:

Col. 12, line 21, "selectively for" should read --selectively--.

Signed and Sealed this

Twenty-first Day of December, 1993

BRUCE LEHMAN

Attest:

Attesting Officer                Commissioner of Patents and Trademarks